United States Patent [19]
Misumi et al.

[11] Patent Number: 5,456,824
[45] Date of Patent: Oct. 10, 1995

[54] APPARATUS FOR SEPARATION OF LIQUID

[75] Inventors: Masashi Misumi, Fuji; Susumu Fujikawa; Nobukazu Tanokura, both of Fujinomiya, all of Japan

[73] Assignee: Terumo Kabushiki Kaisha, Tokyo, Japan

[21] Appl. No.: 186,923

[22] Filed: Jan. 27, 1994

[30] Foreign Application Priority Data

Jan. 29, 1993 [JP] Japan .................................. 5-014325
Jan. 29, 1993 [JP] Japan .................................. 5-014326
Feb. 3, 1993 [JP] Japan .................................. 5-016646

[51] Int. Cl.⁶ .......................... B01D 21/34; B01D 21/26; B01D 12/00
[52] U.S. Cl. .......................... 210/97; 210/109; 210/513; 222/103; 222/214; 604/154
[58] Field of Search .................. 210/86, 90, 94, 210/97, 109, 513, 515, 518; 222/95, 96, 103, 214; 604/155, 154; 422/101

[56] References Cited

U.S. PATENT DOCUMENTS

| | | |
|---|---|---|
| 3,545,671 | 12/1970 | Ross. |
| 4,350,585 | 9/1982 | Johansson et al. ........... 210/94 |
| 4,608,178 | 8/1986 | Johansson et al. ........... 210/744 |
| 4,663,032 | 5/1987 | Loos et al. .................. 210/513 |
| 5,061,451 | 10/1991 | Gänshirt et al. ............ 210/86 |
| 5,135,646 | 8/1992 | Tanokura et al. ........... 210/109 |
| 5,154,716 | 10/1992 | Bauman et al. ............. 604/410 |

FOREIGN PATENT DOCUMENTS

| | | |
|---|---|---|
| 0213469 | 3/1987 | European Pat. Off. . |
| 0484751 | 5/1992 | European Pat. Off. . |
| 55-17585 | 5/1980 | Japan . |

Primary Examiner—John Kim
Attorney, Agent, or Firm—Burns, Doane, Swecker & Mathis

[57] ABSTRACT

An apparatus for extracting liquids different in kind from a flexible primary container storing therein liquid components fractionated into three layers to some satellite containers, by virtue of forming a adhering portion inside the primary container, and communicating with a first outlet and a second outlet, and guiding the upper liquid component to either outlets and the lower liquid component to the remaining outlet.

6 Claims, 13 Drawing Sheets

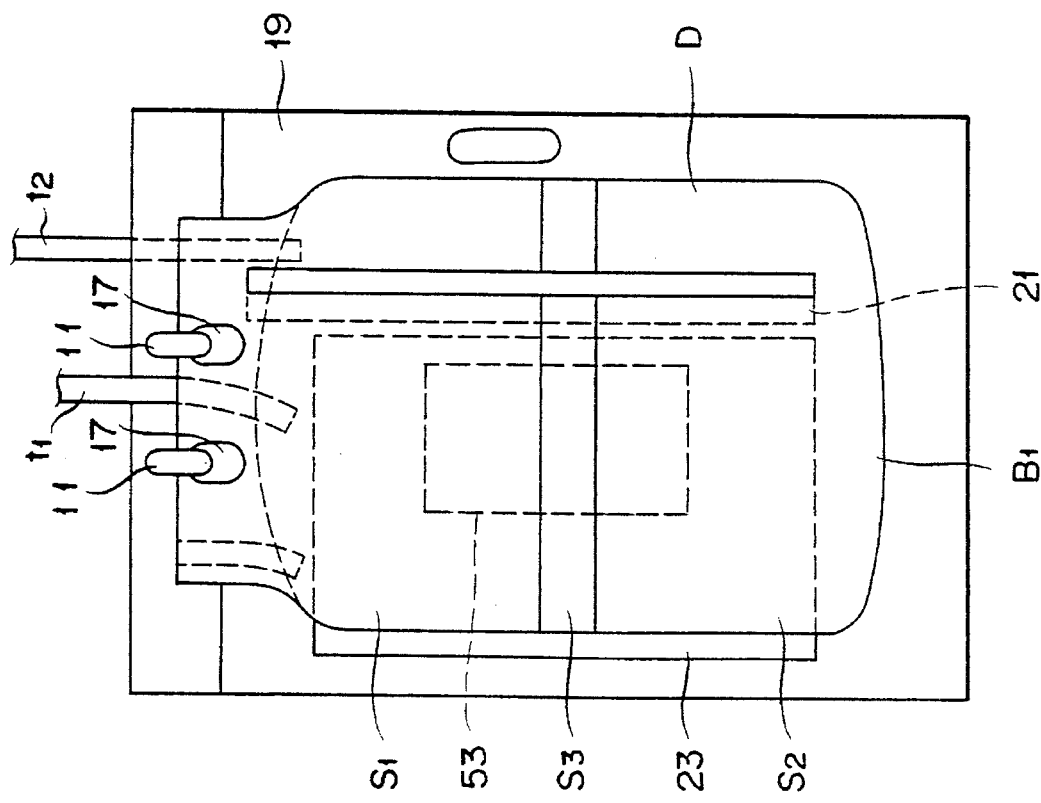

APPARATUS FOR SEPARATION OF LIQUID

BACKGROUND OF THE INVENTION

1. Field of the Invention

This invention relates to a liquid separating apparatus for extracting liquids different in kind from a container such as a blood bag which possesses flexibility and has sealed therein the different liquids separated into plural layers.

2. Description of the Prior Art

Recently, instead of using whole blood for transfusion, the practice of transfusing only necessary blood components to patients in need of such components (componential transfusion) or the practice of collecting only plasma from blood for the purpose of preparing plasma medicines has been in vogue. For the purpose of securing the blood to be used in the componential transfusion or the manufacture of plasma medicines, the flexible blood bag which is popularly called "multiple-bag" has been heretofore used. This blood bag (container) is composed of a blood collecting bag (primary bag) for containing the blood collected from a donor and one or more separation bags (satellite bag) communicating with the primary bag through the medium of a liquid extracting tube (hereinafter referred to simply as "tube"). The blood components separated by the use of a centrifuge and held in the primary bag are extracted independently of each other and transferred into the satellite bags.

When the blood collecting bag is treated with a centrifuge, the blood in the bag is separated into such layers of different components as a plasma layer, a red blood cell layer and an intermediate layer (a soft membranous layer containing platelets, white blood cells etc., so-called buffy coat layer). For these separated blood components to be utilized per se afterward, it is necessary that these components should be collected independently of each other from the blood collecting bag and stored respectively in the separation bags lest they should commingle.

The fractional collection of such blood components has been heretofore accomplished by subjecting the blood bag to the action of a liquid separating device and then compressing the blood bag with pressure exerted on the opposite surfaces thereof thereby allowing the separated components to be transferred into the relevant separation bags through the relevant component extracting tubes which communicate with the blood bag.

The componential extraction of blood is not easily attained by the use of the blood bag of the kind which, as disclosed in JP-A-3-47,266, is provided in the upper part thereof with blood collecting tubes or component extracting tubes. Particularly when the intermediate layer is to be extracted into the satellite bag, it is difficult to choose apt timing for extracting the intermediate layer from the inner wall of the primary bag. Thus the controllability of the blood bag is at a disadvantage and the intermediate layer is apt to remain inthe primary bag.

In the case of the blood bag which, as disclosed in JP-B-63-20,144, is provided with tubes disposed in the upper and lower parts of the primary bag, the componential extraction is attained rather easily. Since the ports to be used for the extraction are disposed at the upper and lower edges of the bag proper, however, the tubes are not handled conveniently during the attachment of the bag to the centrifuge or the blood component separating device.

In the case of the blood bag which, as disclosed in EP-A-0484751A1, is provided with a separation path, ie. a conduit formed in the interior part of the primary bag by bonding or fusion of opposed ribbonlike portions of the inner wall surfaces of the bag, for guiding the liquid of the lower layer to the upper part of the bag proper, the accuracy of collection of red blood cell is decreased in proportion as the width of the path is increased because parts of the plasma component and the intermediate layer component are present besides part of the red blood cell of the lower layer in the path after the step of centrifugal separation. If the width of the path is decreased for the purpose of heightening the accuracy of collection, the uncomfortable possibility arises that the time to be required for the extraction increases and the speed of flow of the blood through the path immensely increases. If the path is endowed with a more or less sizable width, the accuracy of collection of the red blood cell component is lowered. When the blood components fractionally collected by the blood bag using this path of the sizable width are put to use, there ensues the necessity for these components being deprived of impurities by the use of such an instrument as a white blood cell removing filter or a varying adsorbent. The measure of thermally fusing the opposed walls of the primary bag requires formation of a sealed part extending to the bottom part of the bag and results in an increase of steps forming the process of manufacture. During the attachment of the primary bag to the blood separation device, the convenience with which the primary bag is handled is impaired because the portions of the opposed walls of the bag which are available for the attachment are fixed.

By the manner in which the primary bag is compressed after undergoing centrifugal separation, the liquid separating devices are classified into those of the lower biased pressure type disclosed in JP-B-55-17,585 and those of the parallel compression type disclosed in JP-A-55-155,652. The devices of the former type are intended to operate by suspending a primary bag from a hook provided on a separation stand and compressing the suspended primary bag with pressure exerted on the opposite walls of the bag by means of a pressing plate so supported as to render the lower end thereof rotatable and the devices of the latter type by placing a pressing plate parallelly to a separation stand and interposing a primary bag between the separation stand and the pressing plate and pressing the pressing plate across the interposed bag against the separation stand with pressure exerted on the opposite walls of the bag.

Some of these liquid separating devices are adapted to effect the application of pressure automatically or manually. The liquid separating devices capable of automatic application of pressure which have been finding extensive utility, without discrimination between the two types mentioned above, are intended to operate by continuing detection of the position of an intermediate layer by means of an interface sensor and meanwhile compressing the bag by means of a pressing plate.

These conventional liquid separating devices are invariably intended to expel the blood from the bag by the application of pressure to the bag and are not devised to ensure or aid in the discharge of the blood as by altering the shape or construction of the bag itself. Thus, they find utility only in limited applications.

SUMMARY OF THE INVENTION

This invention has been initiated by the urge to solve the problems attendant on the prior techniques as described above. The first object of this invention is to alter the construction of a parent container by compressing the parent container with pressure externally exerted on the outer surfaces of the parent container by the use of a pressing member and enable liquids in desired layers superposed inside the parent container to be readily and infallibly extracted from within the parent container.

The second object of this invention is to provide a liquid separating apparatus which is capable of easy control such as to enable the liquid in the lower layer formed in a container to be extracted through the upper part of the container.

The third object of this invention is to provide a liquid separating apparatus which features simplicity of the handling of tubes and, at the same time, enjoys extremely high accuracy of separation.

To accomplish these objects, this invention provides a liquid separating apparatus comprising a container retaining member for retaining a flexible parent container storing therein liquid components fractionated into at least three layers, i.e. an upper layer, an intermediate layer, and a lower layer, and provided on the side of the upper layer or the lower layer with a first and a second outlet, and a container pressing member composed of a supporting member for supporting one of the two opposite surfaces of the parent container retained by the container retaining member and a pressing member for pressing the parent container, which apparatus is characterized by the fact that the aforementioned pressing member is so constructed as to keep the three regions of the aforementioned upper, intermediate, and lower layers intact, meanwhile expel the aforementioned liquid components from a region intervening between the aforementioned first and second outlets and consequently give rise to a tightly adhering portion on the two opposed surfaces of the parent container and, by virtue of the tightly adhering portion, form inside the parent container a chamber communicating with the aforementioned first outlet and a chamber communicating with the aforementioned second outlet and the aforementioned container pressing portion is so constructed as to guide the liquid component in the upper layer to either of the two outlets and the liquid component in the lower layer to the remaining outlet.

The liquid separating apparatus constructed as described above excels in the ability to control and handle the parent container during the extraction of necessary liquid components from the parent container, effects the separation of liquid components with extremely high accuracy such as to prevent the necessary liquid components being adulterated with unnecessary liquid components at all, and allows generous freedom in the selection of bags to be used for desired separation of liquid components.

The aforementioned pressing member according with this invention comprises a first pressing member and a second pressing member, first drive means adapted to operate the first pressing member so as to retain the three regions of the upper, the intermediate and the lower layer intact, form a substantially tightly adhering portion on the two opposed surfaces of the parent container as extended from between the first and the second outlet across the intermediate layer to a predetermined distance from the other end of the parent container and, by virtue of the tightly adhering portion, produce inside the parent container a large volume portion communicating with the first outlet and a small volume portion communicating with the second outlet, and second drive means adapted to operate the second pressing member so as to press on the large volume portion, guide one of the components in the large volume portion communicating via a common path with the small volume portion formed by the substantially tightly adhering portion to the second outlet and another of the components to the first outlet.

As a consequence, the first pressing member which is driven by the first drive means is allowed to form in the parent container a substantially tightly adhering portion extending from between the first and the second outlet across the intermediate layer to a position separated by a prescribed distance from the other end of the parent container and, by virtue of the tightly adhering portion as a boundary, give rise to a large volume part and a small volume part. When the second pressing member is operated to press on the large volume portion, the one of the components existing in the large volume portion that occupies an area continuing into the common path shared by the large and small volume portions is guided to the second outlet and another of the components is guided to the first outlet.

Alternatively, the aforementioned pressing member according with this invention comprises a pressing member of the general shape of the substantially letter L rotatably supported about an axis extending across the intermediate layer and a second pressing member disposed contiguously to the L-shaped pressing member, drive means adapted to drive the L-shaped pressing member so as to retain the three regions of the upper, the intermediate and the lower layer intact and meantime form a substantially tightly adhering part on the two opposed surfaces of the parent container as extended from between the first and the second outlet across the intermediate layer to a position separated by a prescribed distance from the other end of the parent container and, by virtue of the tightly adhering part, form in the parent container an independent chamber with a large volume portion communicating with the first outlet and an independent chamber with a small volume portion communicating with the second outlet, open the leg of the L-shaped pressing member intersecting the axis thereof to form a path between the large volume portion and the small volume portion by rotating the L-shaped pressing member about the axis thereof, and cause the second pressing member to press the large volume portion and guide the component in the large volume portion now abutting the path to the second outlet.

As a result, a path for guiding the component of a desired layer out of the second outlet can be formed by causing the L-shaped pressing member to press the parent container and, without reference to the type of container, the extraction of the component of the desired layer can be easily effected by the formation of the desired path as described above. When the L-shaped pressing member is so adapted as to press on the front and rear surfaces of the parent container simultaneously, the operation of separation can be carried out smoothly with high accuracy without imparting wrinkles to the parent container.

The aforementioned pressing member according with this invention otherwise comprises a roller type pressing member and a second pressing member disposed contiguously to the roller type pressing member, form a tightly adhering portion on the two opposed surfaces of the parent container as extended from between the first and the second outlet across the intermediate layer to a position separated by a predetermined distance from the other end of the parent container by pressing the roller type pressing member against the parent container and passing the roller type pressing member per se on the parent container in the lateral direction over a predetermined distance from one lateral wall toward the other lateral wall of the parent container while keeping the three regions of the upper, the intermediate, and the lower layer intact and, by virtue of the tightly adhering portion, form in the parent container a path communicating with the second outlet and, by the use of the second pressing member and with the aid of the path, guide the component of the lower layer to the second outlet and, at the same time, guide the component of the upper layer to the first outlet when the upper layer exists on the first outlet and second outlet side or guide the component of the upper layer to the second outlet and, at the same time, guide the component of the lower layer to the first outlet when the lower layer exists on the first outlet and second outlet side.

As a result, the tightly adhering portion can be formed on the two opposed surfaces of the parent container as extended from between the first and the second outlet across the intermediate layer to a position separated by a predetermined distance from the other end of the parent container by pressing the roller type pressing member against the parent container and passing the roller type pressing member per se in the lateral direction over a predetermined distance from one lateral wall to the other lateral wall of the parent container. The tightly adhering portion lends itself to the formation in the parent container of the path communicating with the second outlet. When the second pressing member is operated to press on the parent container, the component of the lower layer is guided to the second outlet and the component of the upper layer is guided to the first outlet when the upper layer exists on the first and second outlet side. By the same token, the component of the upper layer is guided to the second outlet and the component of the lower layer is guided to the first outlet through the path when the lower layer exists on the first outlet and second outlet side.

BRIEF DESCRIPTION OF THE DRAWINGS

FIG. 9 is a rear view of a primary bag illustrating the operation of pressurization by the pressing member.

FIG. 10 is a rear view of a primary bag illustrating the operation of pressurization by the pressing member.

DETAILED DESCRIPTION OF THE PREFERRED EMBODIMENT

Now, the first embodiment of this invention will be described below with reference to the accompanying drawings.

Figure 1:
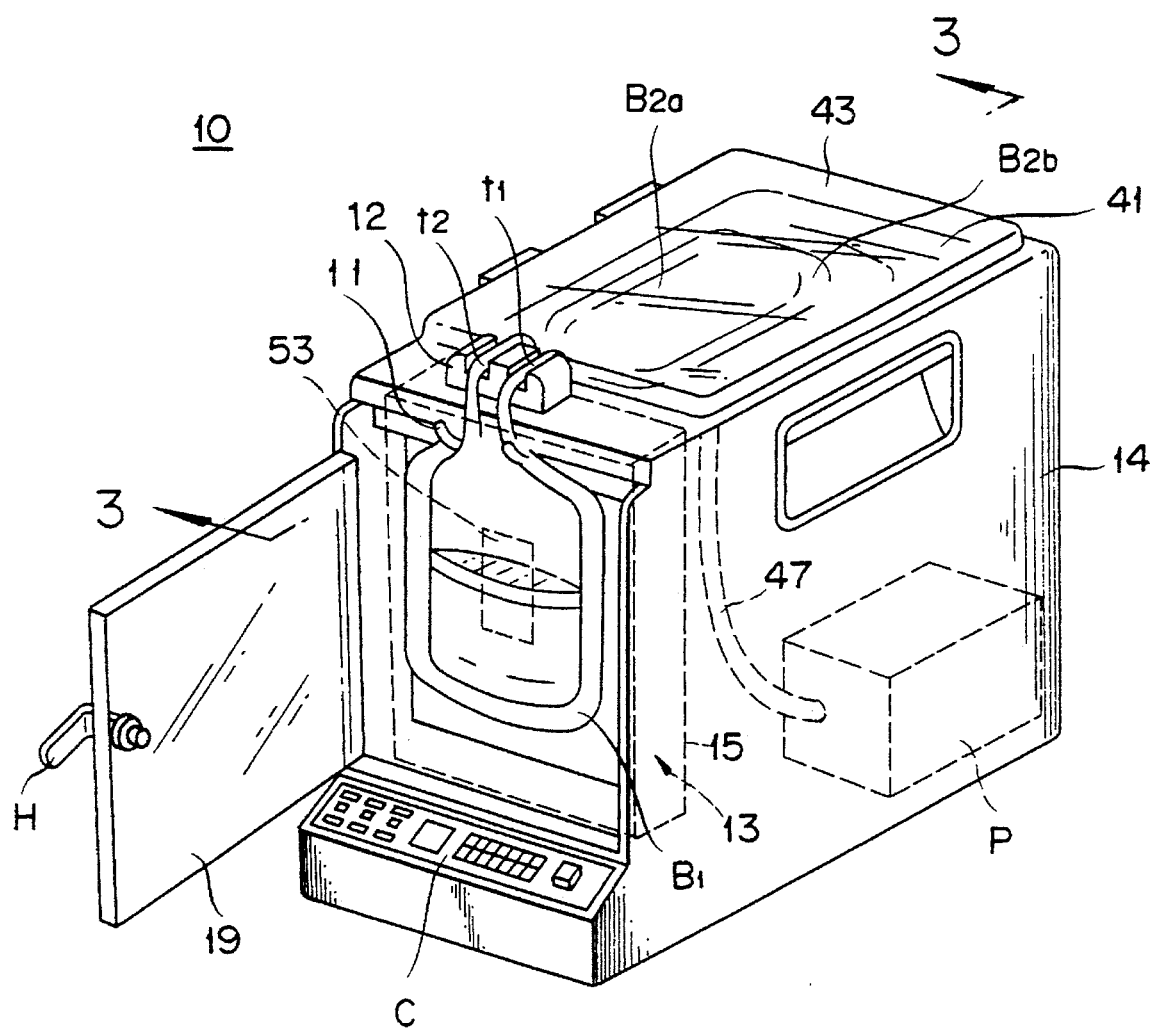
FIG. 1 is a schematic perspective view of a liquid separating apparatus according with the first embodiment of this invention.

In FIG. 1, a liquid separating apparatus 10 fulfills the role of fractionally extracting the blood components from a primary bag (parent container) B1 which has undergone the action of centrifugal separation and comprises a container retaining part or hook 11 for retaining the primary bag B1, a clamp member 12 for selectively clamping tubes t1, t2, a container pressing member 13 for pressing the primary bag B1 retained by the hook 11, and a control unit C for actuating such parts as the container pressing member 13.

Figure 2:
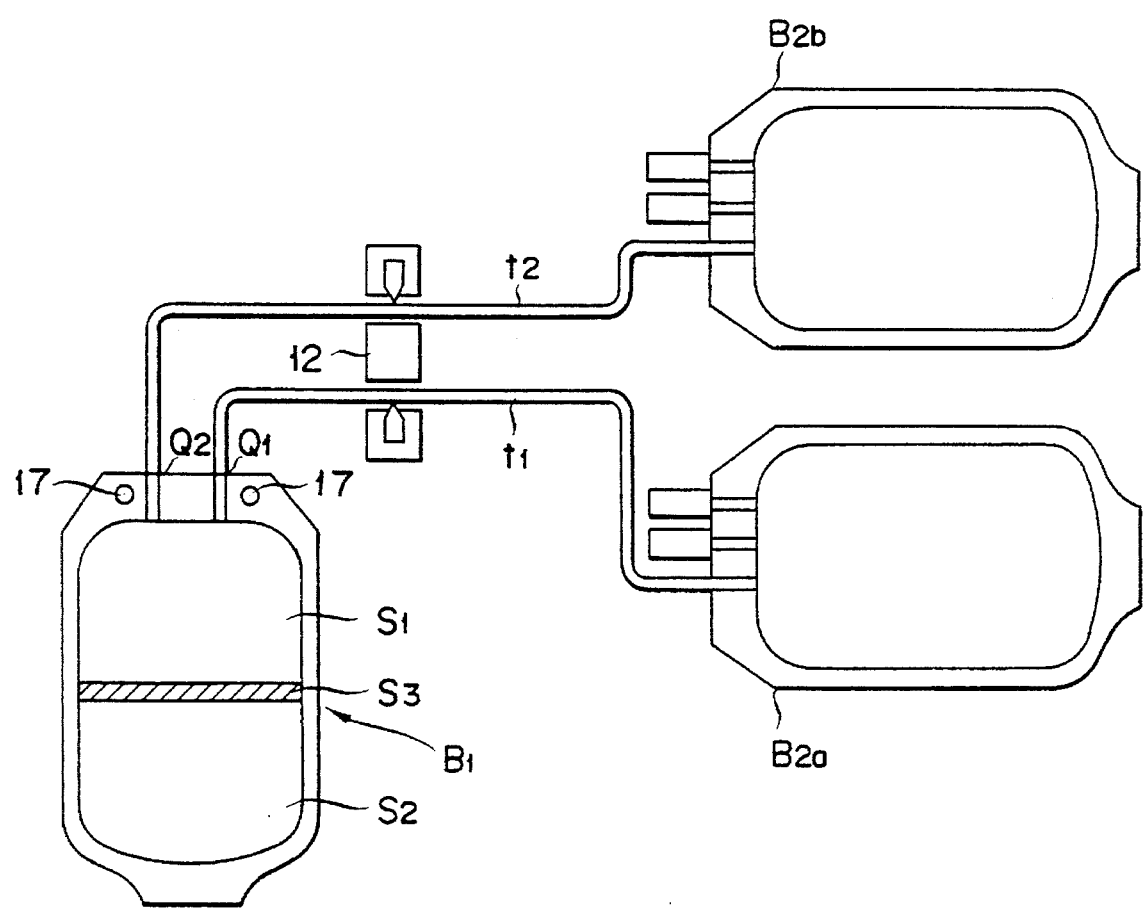
FIG. 2 is a schematic plan view illustrating one example of blood bag.

The primary bag B1 is formed of a flexible synthetic resin and is provided, as illustrated in FIG. 2, with a blood collecting bag or primary bag B1 for storing the blood collected from a donor and a plurality of separation bags or satellite bags B2a, B2b. In the primary bag B1, a first outlet Q1 and a second outlet Q2 are formed. The satellite bag B2a is made to communicate through the tube t1 with the first outlet Q1 and the satellite bag B2b through the tube 62 with the second outlet Q2.

The blood collected in the primary bag B1 is separated into a plasma layer S1, a red blood cell layer S2, and an intermediate layer S3 by centrifugal separation. Then, the plasma layer S1 can be extracted through the tube t1 into the satellite bag B2a and the red blood cell layer S2 through the tube t2 into the satellite bag B2b preparatorily containing a red blood cell preserving liquid while the intermediate layer S3 is left behind in the primary bag B1.

Figure 3:
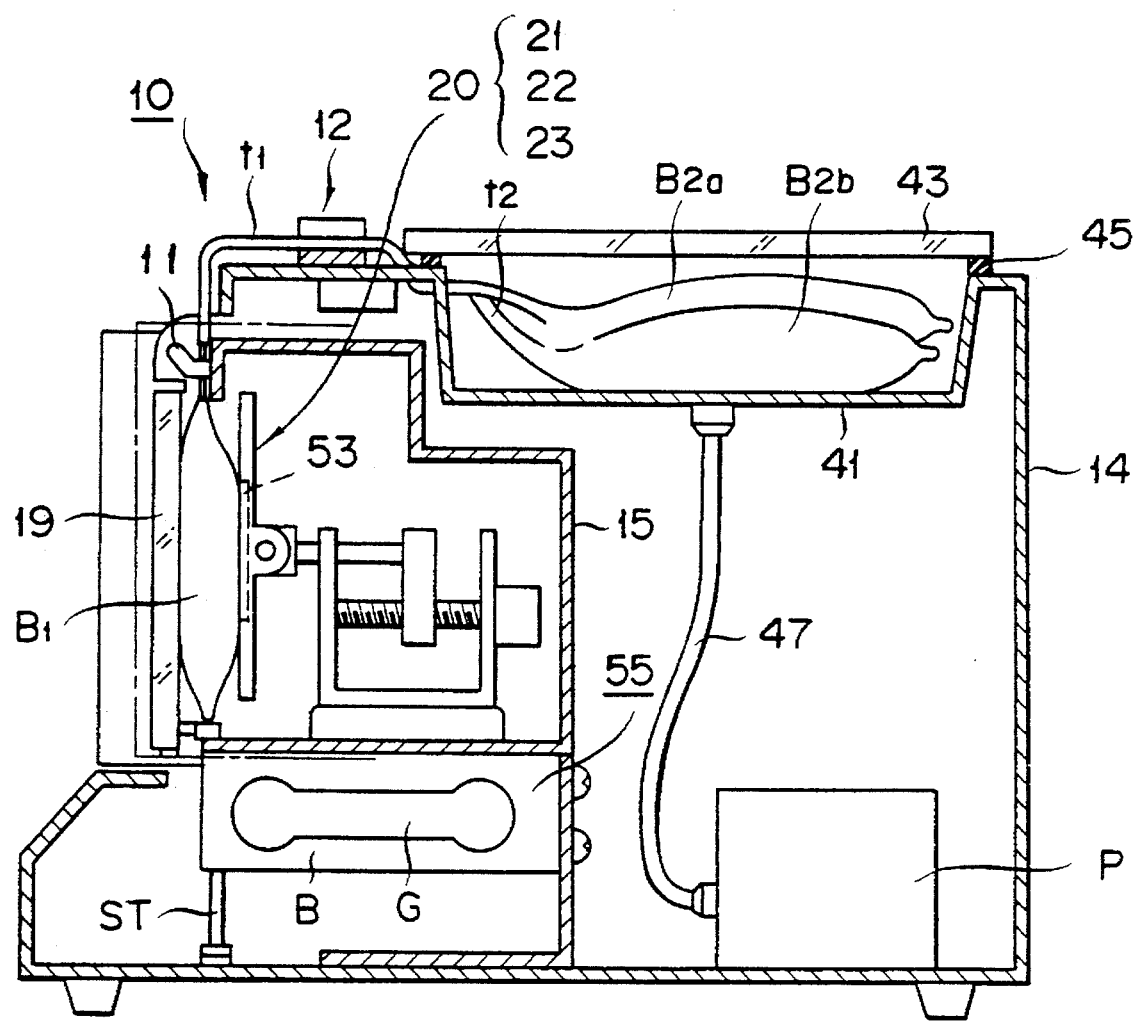
FIG. 3 is a cross section taken through FIG. 1 along the line 3—3.

The container pressing member 13 is disposed inside a housing 15 which is seated in the front part of a main body case 14 as illustrated in FIG. 1 and FIG. 3. The container retaining member, viz. a pair of hooks 11 is projected from the front wall of the housing 15. The primary bag B1 is suspended by inserting through holes 17 formed in the primary bag B1 around the hooks 11 as illustrated in FIG. 2.

To the front surface part of the main body case 14 is attached a swinging door member which is intended to constitute a supporting member 19 as will be specifically described afterward. By opening this door body, the attachment of the primary bag B1 via the through holes 17 to the hooks 11 can be readily attained. By shutting this door member, the primary bag B1 suspended from the hooks 11 can be tightly supported and, at the same time, encased in the housing 15.

The door member is preferably formed of such a transparent material as acrylic resin so that the primary bag B1 held inside of the door member may be seen therethrough distinctly.

In the present embodiment, the door member is utilized as the supporting member 19 which fulfills the role of supporting and pressing the primary bag B1 from the front side thereof. The door member is adapted to press on the primary bag B1 in cooperation with a pressing member 20 disposed inside the housing 15 as illustrated in FIG. 1 and FIG. 3. By using the door member as the supporting member 19 as described above and consequently obviating the necessity of providing an independent pressing, it is allowed to decrease the number of components of the apparatus and simplify the construction thereof.

Figure 4:
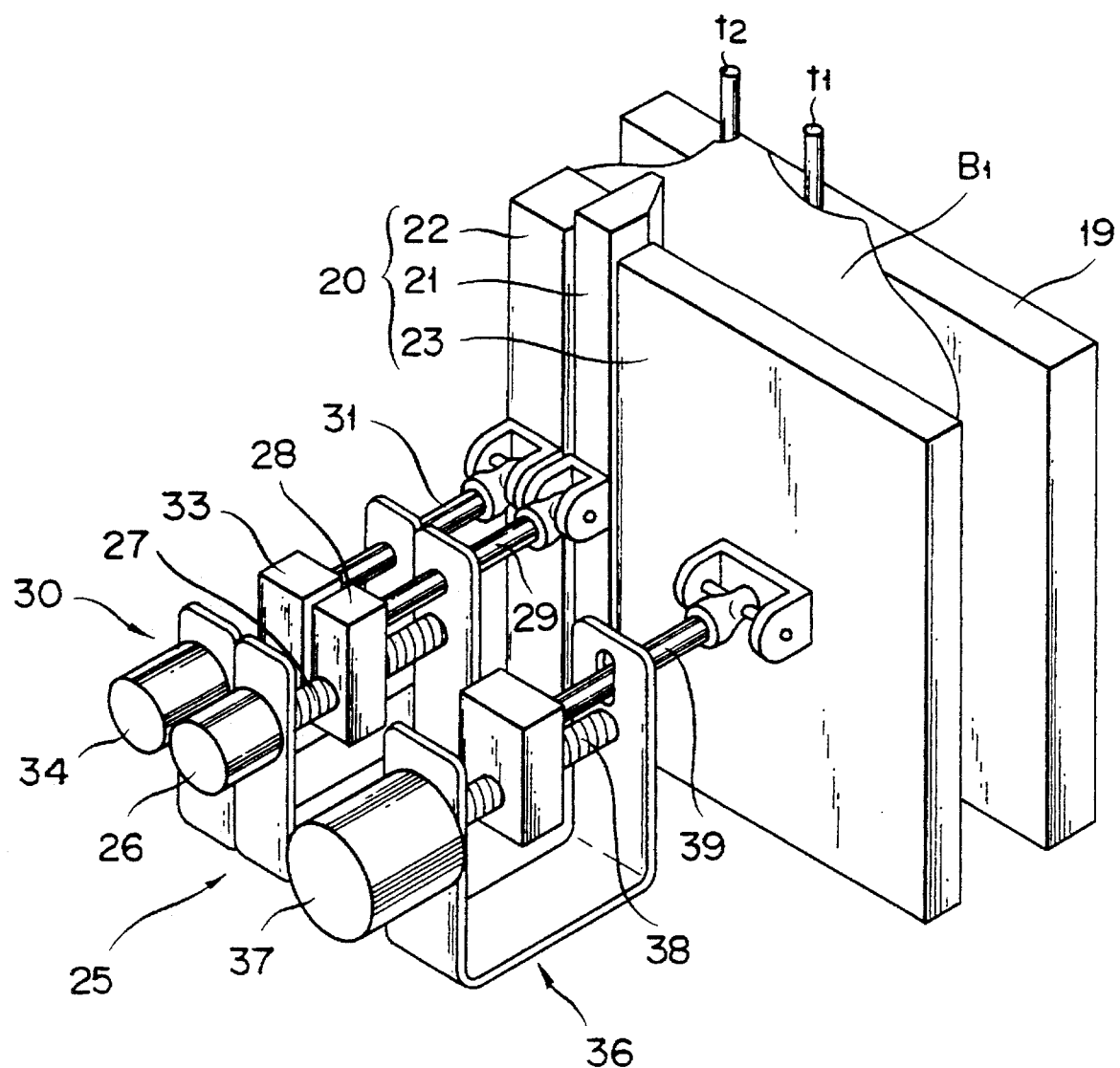
FIG. 4 is a perspective view illustrating a pressing member seated fast in a housing.

The pressing member 20 serving the purpose of pressing the primary bag B1 from the wall surface side thereof is seated inside the housing 15 as illustrated in FIG. 4 and is composed of a first pressing member 21 extended in the substantially vertical direction and adapted to press on the primary bag B1 suspended from the hooks 11 at a position parted from one lateral part of the primary bag B1 by a prescribedpredetermined distance toward the central side of the bag, an auxiliary pressing member 22 serving the purpose of one lateral part of the primary bag B1, and a second pressing member 23 serving the purpose of pressing the primary bag B1 over an area extending from the position contiguous to the first pressing member 21 to the other lateral part of the primary bag B1. These pressing members 21, 22, and 23 are supported by independent supporting members respectively.

The first pressing member 21 is supported by a first supporting member 25 in such a manner as to be freely moved toward or away from the primary bag B1 as illustrated in FIG. 4. The first supporting member 25 is possessed of a first ball screw 27 which is rotated by a first drive motor 26. When the first ball screw 27 is rotated, a first moving body 28 is moved back and forth along the first ball screw 27. To this first moving body 28 is attached a first reciprocating bar 29 which swingably supports the first pressing member 21 thereon. As a result, the first pressing member 21 is moved toward or away from the primary bag B1 when the first ball screw 27 is rotated by the first drive motor 26. Incidentally, the oscillation plane of the first pressing member 21 is substantially vertical and coincident with the direction of the forward and backward motion.

Optionally, a spring member (not shown) may be provided herein for the purpose of keeping the first reciprocating bar 29 urged constantly toward the primary bag B1 thereby preventing the first ball screw 27 from producing play.

An auxiliary supporting member 30 for supporting the auxiliary pressing member 22 is substantially similar in construction to the first supporting member 25. An auxiliary reciprocating bar 31 for supporting the auxiliary pressing member 22 is attached to an auxiliary moving body 33 which is moved back and forth along the auxiliary ball screw by the rotation of an auxiliary ball screw (not shown). The auxiliary pressing member 22, therefore, is moved toward or away from the primary bag B1, kept substantially parallel to the supporting member 19, when the auxiliary ball screw is rotated by an auxiliary drive motor 34 of the auxiliary supporting member 30.

The second pressing member 23 is also connected to a second supporting member 36 which is substantially similar in construction to the first supporting member 25. The second pressing member 23, therefore, is moved toward or away from the primary bag B1, kept substantially parallel to the supporting member 19, when a second ball screw 38 is rotated by a second drive motor 37 of the second pressing member 23.

Incidentally, in the present embodiment, the pressing members 21, 22, and 23 supported independently by the supporting parts are adapted to be moved back and forth as held in a freely swingable state. Optionally, the lower ends or upper ends of the pressing members 21, 22, and 33 may be supported in a swingable manner. The drive means for these supporting parts are not particularly limited to a motor. Hydraulic or pneumatic cylinders may be used instead. It is otherwise permissible to use solenoid valves for driving the supporting members.

On the main body case 14 is disposed a tray 41 for storing the satellite bags B2a, B2b which are connected to the primary bag B1 through the tubes t1, t2 as illustrated in FIGS. 1 and 3. This tray 41 has an opening that is shut with an upper lid 43. The periphery of the upper lid 43 abutting the tray 41 is hermetically sealed with a packing 45. Thus, the interior of the tray 41 can be evacuated by a pump P and a conduit 47. This evacuation aids in facilitating the inflow of the blood components from the primary bag B1 to the satellite bags B2a, B2b.

Figure 5:
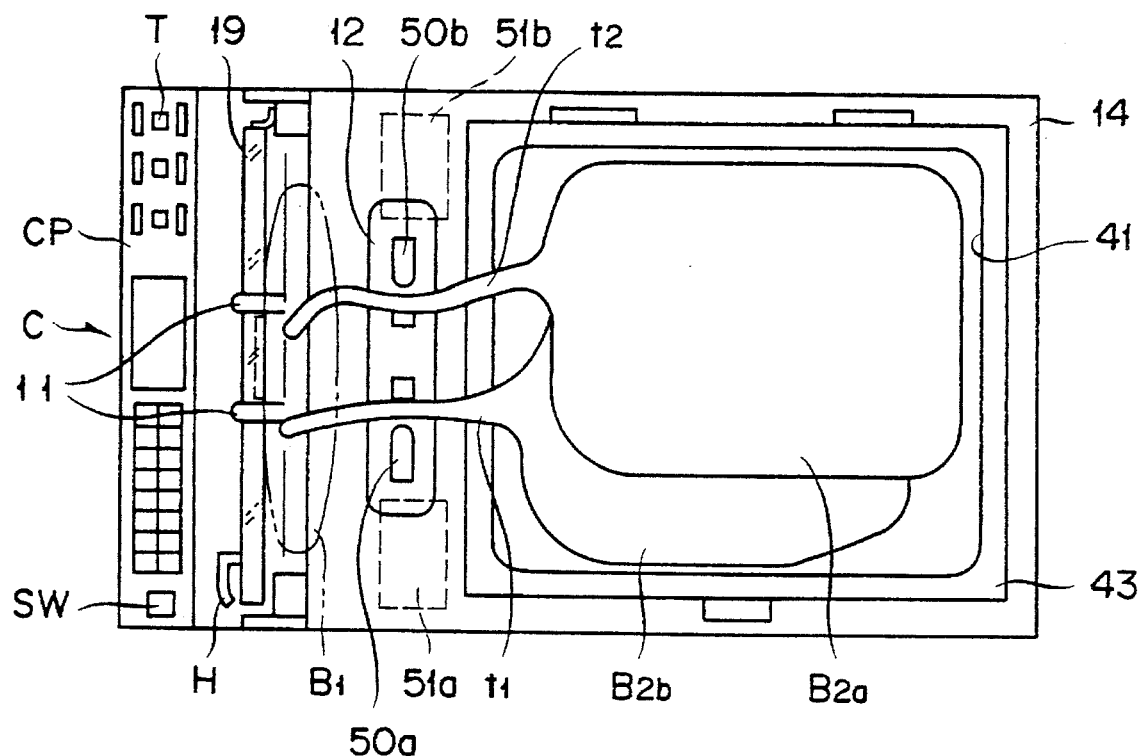
FIG. 5 is a horizontal cross section illustrating the essential part of the apparatus of FIG. 1.

Further, on the main body case 14 is disposed the clamp member 12 which serves the purpose of stopping or allowing selectively and independently the flow of blood components through the two tubes t1, t2 extended from one end part of the primary bag B1 as illustrated in FIGS. 1 and 5. This clamp member 12 is composed of a first clamp member 50a for opening or shutting the tube t1 offering the interior thereof for the conveyance of the plasma component and a second clamp member 50b for opening or shutting the tube t2 offering the interior thereof for the conveyance of the red blood cell component. The clamp member 12 is also provided with solenoids 51a, 51b which actuate the clamp members 50a, 50b respectively. These solenoids 51a, 51b are adapted to receive signals issued from the control unit C and, based on the signals, selectively and independently open or shut the clamp members 50a, 50b.

By controlling the operation of opening or shutting the clamp members 50a, 50b as described above, the flow volumes through the tubes t1, t2 of the blood components in transit from the primary bag B1 to the satellite bags B2a, B2b can be controlled. Meanwhile the intermediate layer S3 or buffy coat layer which is eventually discharged can be left behind inside the primary bag B1.

The signals from the control unit C are to be issued in accordance with such factors as the position of the intermediate layer S3, the weight of the primary bag B1 and/or the satellite bags B2a, B2b, and the duration of pressurization by the second pressing member 23. Thus, these factors must be continuously measured.

The position of the intermediate layer S3 is detected by an interface detecting member 53 which is attached to the second pressing member 23. Generally, a photosensor is used as the interface detecting member 53, which is adapted to detect the positions of interfaces between the aforementioned three layers by virtue of the differences of the layers in light absorbance. The signals from the interface detecting member 53 are input into the control unit C.

A weight sensor 55 disposed below the container pressing part 13 constitutes a weight determining part for measuring the weight of the primary bag B1. It is adapted to calculate the weight of the primary bag B1 by subtracting the predetermined tare weight of the housing 15, supporting member 19, the pressing member 20, etc. from the total weight of the aforementioned container pressing member 13 determined by the weight sensor 55. Then, the signals from this weight sensor 55 are input into the control unit C. The weight sensor 55 may be composed of an aluminum block B disposed so as to support the housing 15 of the container pressing member 13 and a strain gauge G attached to the lateral surface of the aluminum block B. The symbol "ST" found in FIG. 3 stands for a balance stopper.

A timer T provided on a control panel CP of the main body case 14 fulfills the role of detecting the duration of the pressurization by the second pressing member 23 on the primary bag B1. The information on the duration of pressurization is input from the timer T to the control unit C.

Now, the operation of the first embodiment will be explained below.

First, the supporting member 19 is to be kept in the opened state as illustrated in FIG. 1. Then, the primary bag B1 is set in place by inserting the through holes 17 of the primary bag B1 around the hooks 11 and, at the same time, the tubes t1, t2 extended from the primary bag B1 are inserted respectively in the clamp members 50a, 50b, the satellite bags B2a, B2b are mounted on the tray 41, and the upper lid 43 is shut. The blood inside the primary bag B1 has been already separated into the upper layer (plasma layer), the intermediate layer, and the lower layer (red blood cell layer) by the use of a centrifuge.

After the primary bag B1 has been set in place inside the housing 15 as described above, a start switch SW of the control unit C shown in FIG. 5 is turned on. The two clamp members 50a, 50b are kept in the shut state by the solenoids 51a, 51b.

When the start switch SW is turned on, first the timer T is set and the primary bag B1 is weighed. The weight of the primary bag B1 is calculated by subtracting the tares such as of the housing 15 and the pressing member 20 from the total weight of the container pressing member 13. To be specific, this calculation is effected by subtracting the tare weight of the container pressing member 13 stored in advance in the control unit C from the weight of the container pressing member 13 detected by the weight sensor 55.

When the weight of the primary bag B1 falls short of the predetermined weight, the primary bag B1 is rejected as unfit. When the primary bag B1 has the predetermined weight and is rated as fit, the supporting member 19 in the form of a door is shut.

Figure 6:
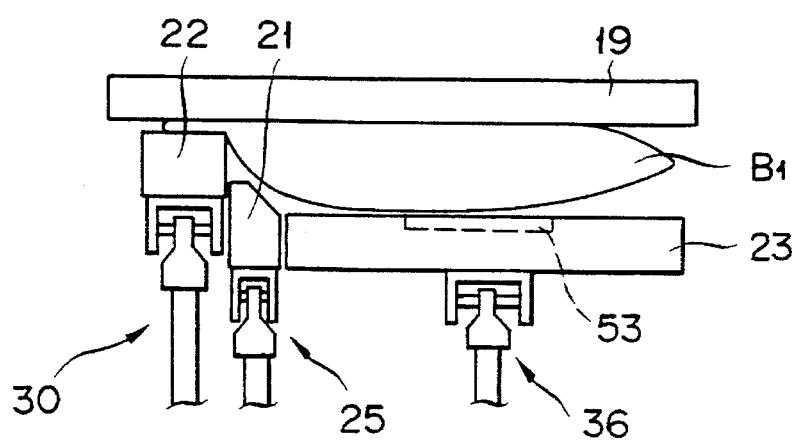
FIG. 6 is a planar cross section illustrating the operation of pressurization by a pressing member.

When the supporting member 19 is shut, the auxiliary drive motor 34 is actuated and the auxiliary pressing member 22 is moved toward the primary bag B1, kept substantially parallel to the supporting member 19. By the cooperation between the auxiliary pressing member 22 and the supporting member 19, the front surface side of the primary bag B1 now abutting the auxiliary pressing member 22 is pressed substantially tightly against the rear surface side thereof as illustrated in FIG. 6. The liquid is expelled from the part of the primary bag B1 in which the substantially tight adhesion has occurred.

The auxiliary pressing member 22 which is shown in the diagram presses one lateral part of the primary bag B1 over a length from the upper end to the lower end thereof. It is permissible to position the lower end part of the auxiliary pressing member 22 at a level higher than that of the lower end part of the primary bag B1 similarly to the first pressing member 21.

Figure 7:
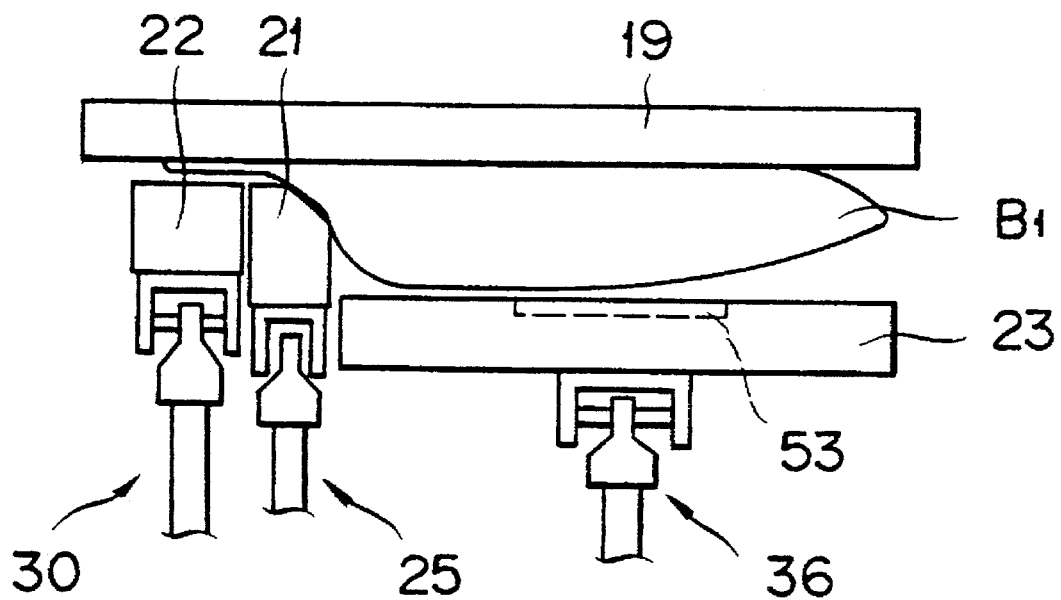
FIG. 7 is a planar cross section illustrating the operation of pressurization by the pressing member.

After the pressurization by the auxiliary pressing member 22 is completed, the first drive motor 26 is actuated to move the first pressing member 21 toward the primary bag B1 and cause the front surface side abutting the first pressing member 21 to be tightly pressed against the rear surface side thereof by the cooperation of the first pressing member 21 and the supporting member 19. As a result, in one lateral part of the primary bag B1, the front and rear surface sides of the primary bag B1 are brought into substantially tight contact by the first pressing member 21, the auxiliary pressing member 22, and the supporting member 19 as illustrated in FIG. 7. The operations of the two pressing members 21, 22 for the creation of this substantially tight contact may occur substantially simultaneously. Since the parts connecting the two pressing members 21, 22 to the reciprocating bars 29, 31 are so positioned as to balance vertically the weights of the pressing members 21, 22, the longitudinal directions of the pressing members 21, 22 are paralleled to the supporting member 19 through self-adjustment when the primary bag B1 containing a fluid substance is pressed. In the part of the primary bag B1 in which the front and rear surface sides thereof are tightly pressed against each other, therefore, the tight contact occurs substantially simultaneously. It is naturally permissible to have the two pressing members 21, 22 supported swingably at the respective upper parts thereof similarly to the supporting member 19.

Figure 8:
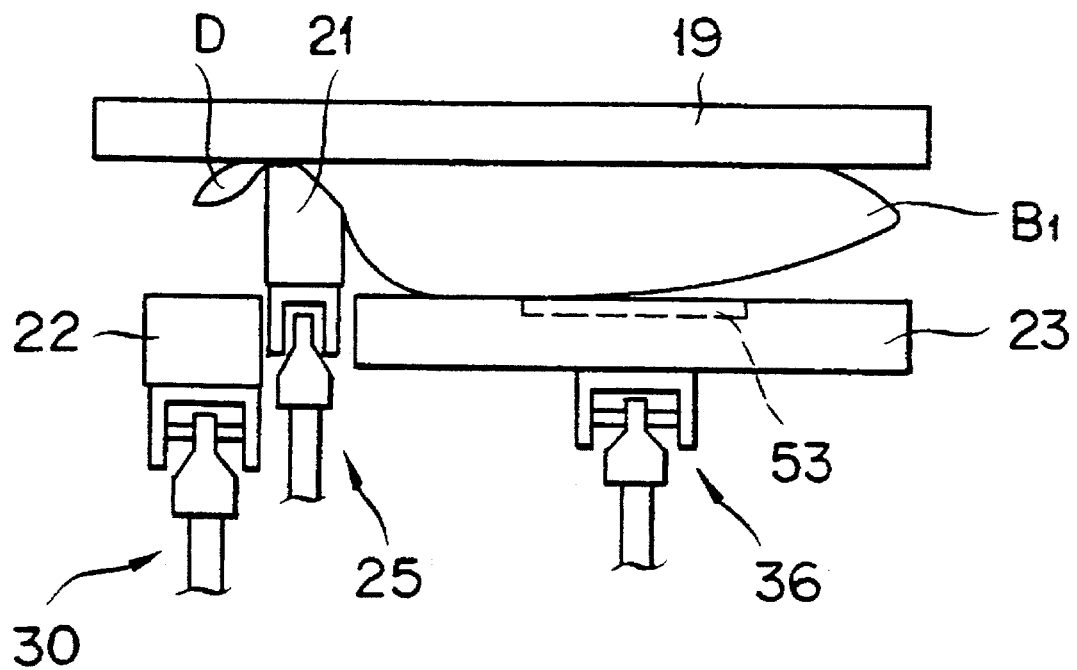
FIG. 8 is a planar cross section illustrating the operation of pressurization by the pressing member.

When the front and rear surface sides of the primary bag B1 are brought into substantially tight contact by the first and auxiliary pressing members 21, 22 as described above, then the auxiliary drive motor 34 is actuated to move the auxiliary pressing member 22 away from the primary bag B1. As a result, a path D for guiding the liquid of the lower layer S2 to the second outlet Q2 is formed on one lateral part of the primary bag B1 as illustrated in FIG. 8 and FIG. 9.

Incidentally, since the lower end part of the first pressing member 21 is positioned at a level higher than that of the lower end part of the primary bag B1 as illustrated, the path D which is formed as described above is allowed to communicate with the lower layer S2.

For the purpose of securing the communicating part between the path D and the lower layer S2 as described above, the lower end part of the first pressing member 21 is desired to be positioned at a level higher than that of the lower end part of the primary bag B1. The position of the intermediate layer S3 is not constant. When the lower end of the first pressing member 21 is positioned at the higher level as described above, the possibility ensues that the pressure of the first pressing member 21 will fail to divide the intermediate layer S3 into two parts or the liquid of the intermediate layer S3 will flow into the path D when the liquid of the lower layer S2 is discharged from the second outlet Q2 via the path D. The position of the lower end part of the first pressing member 21, therefore, is desired to be set at the lowest possible level on the condition that the communicating part between the path D and the lower layer S2 is secured infallibly.

Further, the auxiliary pressing member 22 which is used in the present embodiment may be omitted. In the absence of this auxiliary pressing member 22, when the supporting member 19 is shut, the first pressing member 21 is immediately moved toward the primary bag B1 by the first drive motor 26 and, by the cooperation of the first pressing member 21 and the supporting member 19, the substantially tight adhesion of the front surface side to the rear surface side and the formation of the path D on one lateral part of the primary bag B1 are effected in the same manner as described above. In this case, the consequently formed path D is fated to accommodate the liquids of the upper layer S1 and intermediate layer S3, though both in minute amounts, as illustrated in FIG. 10. Prior to the extraction of the liquid of the lower layer S2 from the primary bag B1, therefore, it is desirable first to evacuate the path D of the liquids of the upper layer S1 and intermediate layer S3 and then extract the liquid of the lower layer S2 through the second outlet Q2 and store it in the satellite bag B2b.

After the path D for guiding the liquid of the lower layer S2 to the second outlet Q2 has been formed on one lateral part of the primary bag B1, the second drive motor 37 is actuated to oscillate the second pressing member 23 and, in cooperation with the supporting member 19, press on the primary bag B1. Since the door or the supporting member 19 is formed of a substantially transparent material, the operator can visually observe the primary bag B1 which is now in the pressed state.

When the supporting member 19 and the second pressing member 23 begin to press on the primary bag B1, the vacuum pump P is actuated and the interior of the tray 43 given negative (evacuated) pressure. Preferably the blood components are desired to be smoothly transferred to the satellite bags B2a, B2b as described above.

So long as the pressurization on the primary bag B1 is present, the plasma component of the upper layer S1 is transferred through the first outlet Q1 to the satellite bag B2a and the red blood cell component of the lower layer S3 is forwarded via the path D and transferred through the second outlet Q2 to the satellite bag B2b. During the separation of these blood components, the position of the intermediate layer S3 in the primary bag B1 is detected by the interface detecting member 53, the weights of the bags B1, B2a, and B2b are detected by the weight sensor 55, and the duration of the pressurization is constantly detected by the timer T.

In short, the interface detecting member 53 fulfilling the role of detecting the position of the intermediate layer S3 determines whether or not the intermediate layer S3 is positioned within a predetermined range. When the position of the intermediate layer S3 remains within this range, the two clamp members 50a, 50b continue to be in their existing open-shut states. When the position of the intermediate layer S3 rises past the upper limit of the range, the open-shut states of the clamp members 50a, 50b are adjusted or reversed so that the position returns into this range. By thus controlling the position of the intermediate layer S3 so that it may constantly remain at a generally intermediate level within the primary bag B1, the plasma component and the red blood cell component are transferred into and stored in the satellite bags B2a, B2b and the intermediate layer S3 is left behind in the primary bag B1.

When the weights of the primary bag B1 and the satellite bags B2a, B2b reach the predetermined levels, the two clamp members 50a, 50b are shut and the outflow of the blood components is stopped.

The detection of the pressure in the tray 43 is intended to smooth the outflow of the blood components to the satellite bags B2a, B2b. When the interior of the tray 43 fails to assume the predetermined negative (evacuated) pressure, the pressurization on the primary bag B1 is discontinued as a errored pressure. Optionally, the duration of pressurization which is detected by the timer T may be displayed on the control panel CP formed in front face of the main body case 14.

After the blood components have been extracted from the primary bag B1 and transferred to the satellite bags B2a, B2b as described above, the two clamp members 50a, 50b are shut and the vacuum pump P and the weight determining devices are stopped. Subsequently, the tubes t1, t2 are shut with such as clips, the door is opened, and the primary bag B1 and the satellite bags B2a, B2b are removed from the liquid separating apparatus. When the supporting member 19 in the form of a door is opened at this time, the first, auxiliary, and second pressing members 21, 22, and 23 are moved away from the primary bag B1 and the container pressing part 18 assumes the stand-by state for pressurization, namely the initial state.

Figure 11:
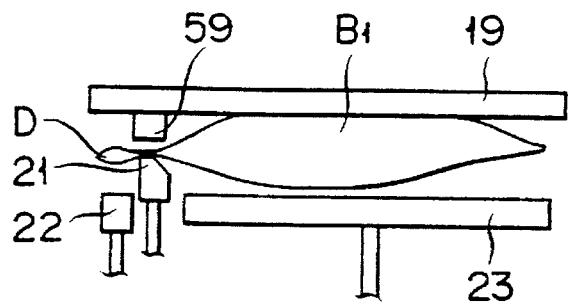
FIG. 11 is a plan view illustrating a modified example of supporting member.

The supporting member 19 may have a pressure auxiliary member 59 attached to the inner surface thereof as shown in FIG. 11. The attachment of the pressure auxiliary member 59 in the manner described above permits a decrease in the amount of deformation which occurs in the primary bag B1 when the first pressing member 21 is attached fast to the primary bag B1 on the condition that the shape of the primary bag B1 is such as to symmetrize the front and rear surface sides thereof.

The pressing member 20 used in the embodiment cited above is depicted as one possessing a substantially rectilinearly extending shape. This invention does not need to use this particular shape for the pressing member 20. The pressing member 20 may be in any of the shapes shown in FIGS. 12 to 15. In the diagrams of FIGS. 12 to 15 and those of FIGS. 1 to 11, like parts are represented by like reference numerals.

Figure 12:
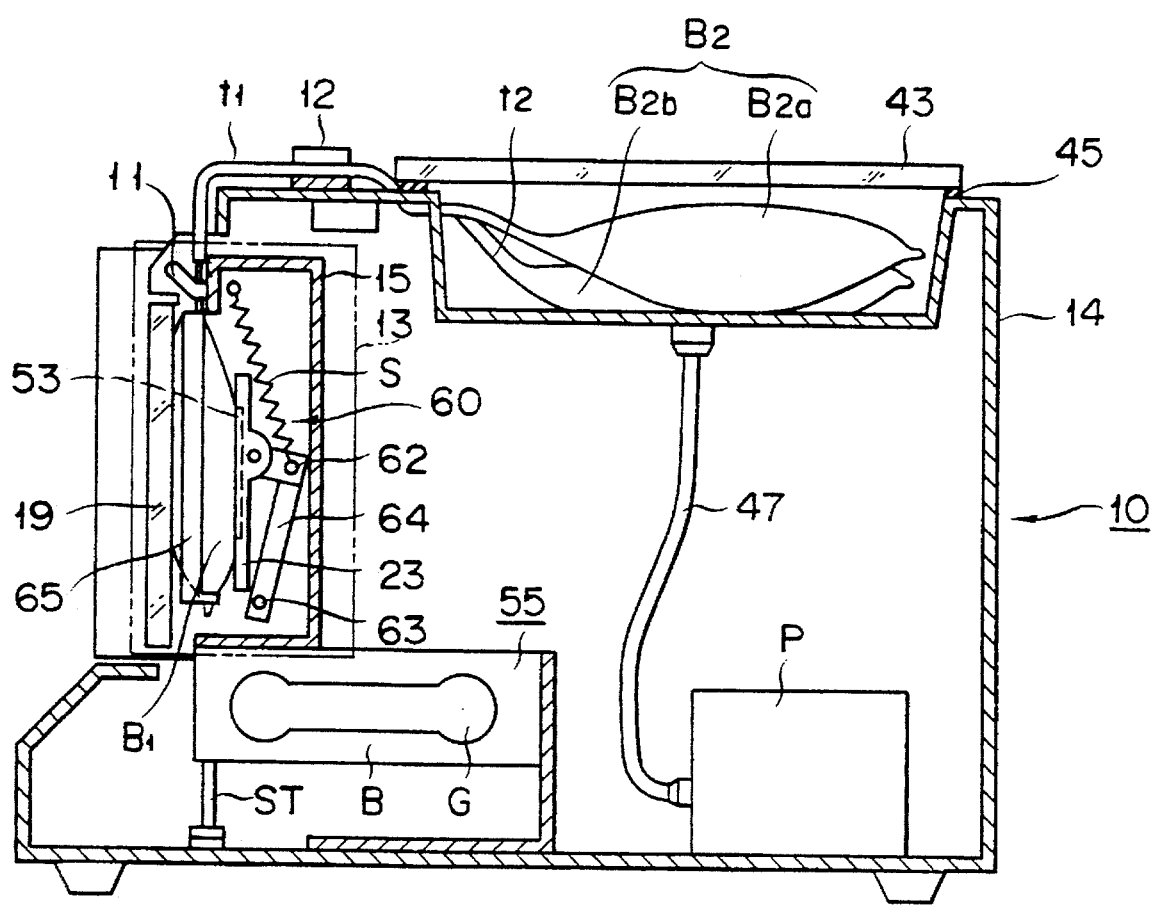
FIG. 12 is a schematic cross section of a liquid separating apparatus according with the second embodiment of this invention.

A container pressing member 13 used in this embodiment is provided in the interior thereof with a supporting member 19 which contacts the front surface side of the primary bag B1 and assumes a stationary state during the pressurization, a pressing body 60 which collides with the rear surface side of the primary bag B1, a spring member S which exerts pressure so that the pressing body 60 will press the primary bag B1 or move toward a supporting member 19, and a pressing member 61 corresponding to the first pressing member 21 as illustrated in FIG. 12.

The pressing body 60 mentioned above is provided with a pressing plate 23 which is disposed inside a housing 15 in opposed relation to the supporting member 19. A first link 62 is rotatably connected to the rear surface side of the pressing plate 23. To the rear end of this first linkmember 61 is connected the end part of a second link member 64 rotatably supported by a supporting shaft 63 which is attached to the housing 15 mentioned above.

Figure 13:
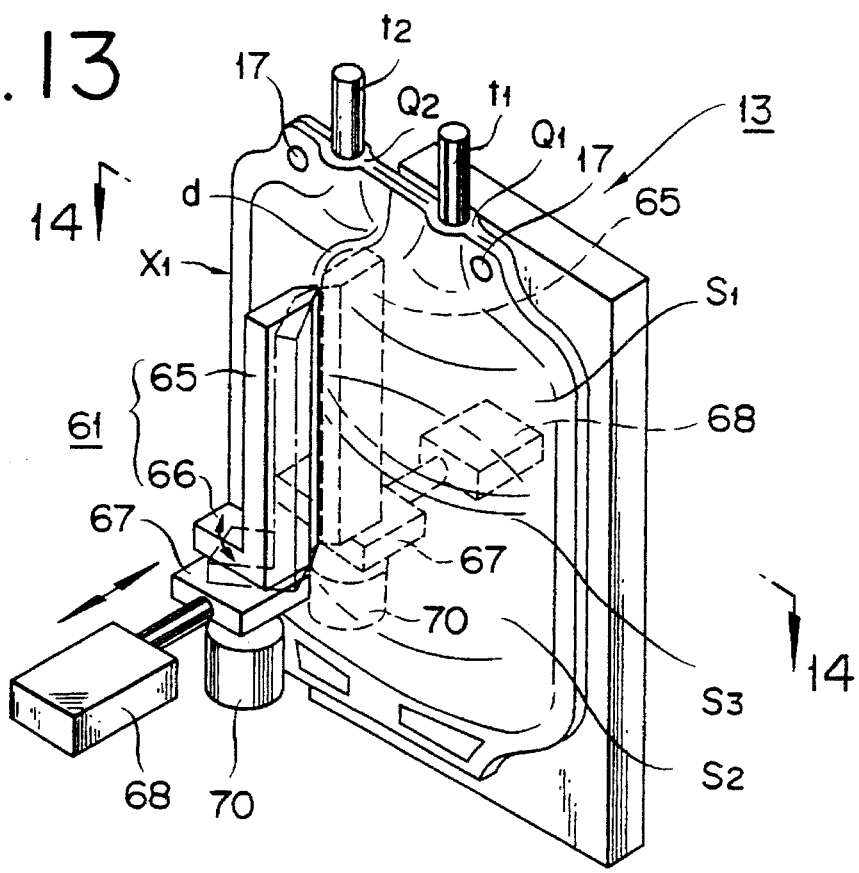
FIG. 13 is a perspective view illustrating the essential part of the apparatus of FIG. 12.
Figure 14:
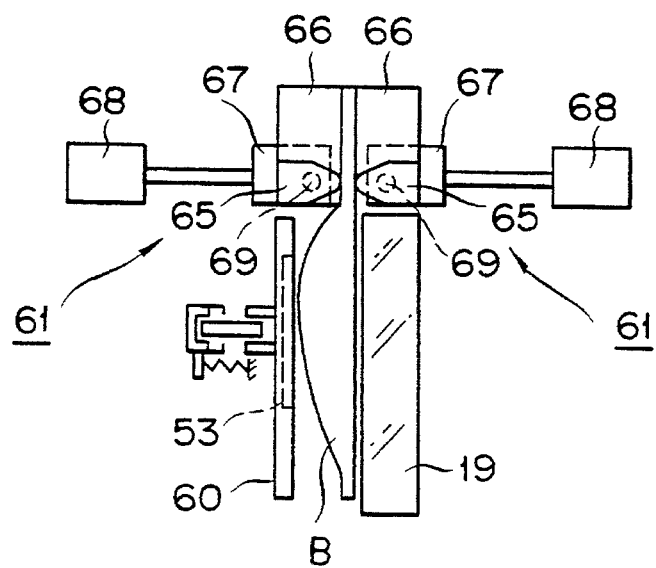
FIG. 14 is a schematic cross section taken through FIG. 13 across the line 14—14.

Particularly, the pressing member 61 of this embodiment, as illustrated in FIGS. 13 and 14, is provided inside the container pressing member 13 encased in the housing 15 with a platelike first pressing member 65 which is capable of forming at a position on the extension of the terminal of a seal part d provided in the primary bag B1 a path D for guiding the red blood cell layer S2 through a second outlet Q2 when tight contact is formed between the front and rear surface sides of the primary bag B1 and a platelike second pressing member 66 which is integrally attached to the first pressing member 65. Since the pressing member 61 which comprises the first pressing member 65 and the second pressing member 66 is formed by imparting the shape of an inverted L and the shape of an L respectively to plate materials, it will be referred to briefly as a substantially L-shaped member 61 hereinafter.

To this first pressing member 65 is attached a reciprocating body 67 capable of moving back and forth. The reciprocating body 67 is adapted to be actuated by a cylindrical member 68. A rotary shaft 69 which is fitted with the reciprocating body 67 and formed in an extended shape is connected to the lower surface of the second pressing member 66. A shaft rotating member 70 such as a rotary solenoid is attached to the end part of the rotary shaft 69. The part of the first pressing member 65 which contacts the primary bag B1 is desired to have a shape edge which is capable of producing an ample pressing force and perfectly sealing the formed path D from the other parts.

The substantially L-shaped member 61 mentioned above operates as follows.

Figure 15:
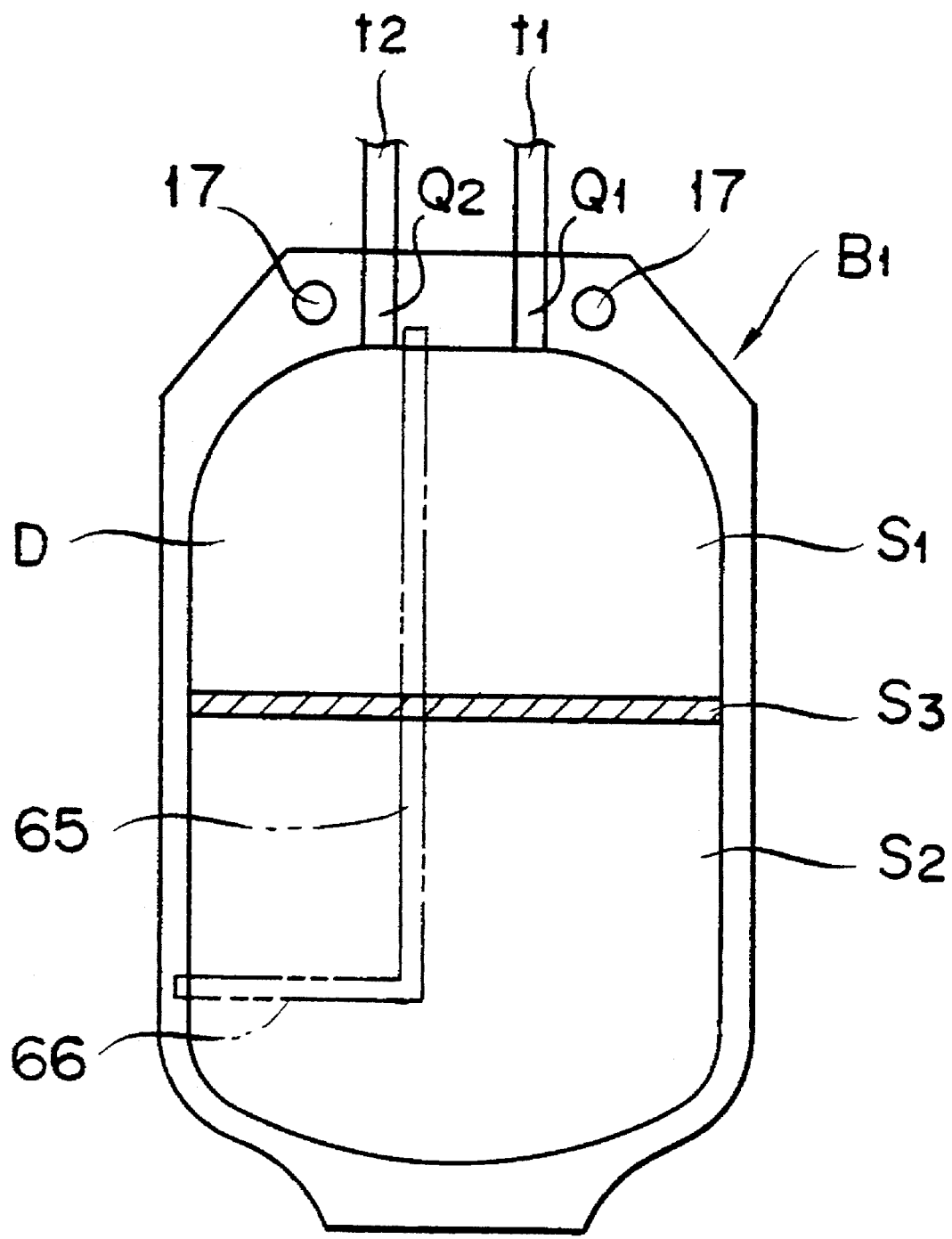
FIG. 15 is a front view illustrating the state in which the bag is pressed in the apparatus of FIG. 12.

First, the substantially L-shaped member 61 causes the opposed front and rear surfaces of the primary bag B1 to produce a tightly adhering portion extending from between the first outlet Q1 and the second outlet Q2 across the intermediate layer S3 to a position separated by a predetermined distance from the lower end of the primary bag B1 while keeping the three regions of the plasma layer S1, the red blood cell layer S2, and the intermediate layer S3 intact. At the same time, the generally L-shaped member 61, by virtue of the tightly adhering portion, forms inside the primary bag B1 an independent chamber of the large volume portion communicating with the first outlet Q1 and an independent chamber of the small volume portion communicating with the second outlet Q2. The substantially L-shaped member 61 is rotatably supported around an axis extending in the direction intersecting the intermediate layer S3 (substantially vertical direction in the diagram). When the substantially L-shaped member 61 is rotated by the drive means 70, the second pressing member 66 is released and a path D is formed between the large volume portion and the small volume portion as illustrated in FIG. 15. The pressing body 60 mentioned above is so adapted as to press the large volume portion of the primary bag B1 and guide the component of the large volume portion adjoining the path D to the second outlet Q2.

The position (height) of the second pressing member 66 is not particularly limited. Since the apparatus has for its object the collection of blood components with extremely high accuracy, however, the position of the lower end is desired to fall within the size of the red blood cell layer S2. Then, when the substantially L-shaped member 61 has formed the path D, the component of the plasma layer S1 can be immediately extracted through the first outlet Q1 without being adulterated with the component of the intermediate layer S3. When the intermediate layer S3 shortly rises past the entrance of the path D, the second pressing member 66 is opened so as to permit the component of the red blood cell layer S2 to be extracted through the second outlet Q2. The possibility of the intermediate layer S3 mingling with the components of the plasma layer S1 and the red blood cell layer S2, therefore, is nil.

Further, by alternating the extraction of the component of the plasma layer S1 and the extraction of the component of the red blood cell layer S2 at a fixed interval, the amount of vertical movement of the intermediate layer S3 can be minimized and, therefore, the possibility of the intermediate layer S3 mingling into the plasma layer S1 and the red blood cell layer S2 can be precluded, and the accuracy of detection by the interface detecting member 53 mentioned above can be heightened.

The pressing body 60 may be adapted so that it will be pressed against the primary bag B1 and per se passed on the primary bag B1 as far as the seal portion d of the primary bag B1. In this case, the substantially L-shaped member 61 mentioned above must be supported on a base plate and provided with a horizontally moving unit capable of moving the base plate by the use of moving means (not shown). In consequence of this modification, the first pressing member 65 of the substantially L-shaped member 61 can be exclusively moved in the lateral horizontal direction of the primary bag B1 from the lateral end part of the primary bag B1 to between the first outlet Q1 and the second outlet Q2 as pressed in the vertical direction against the primary bag B1. As a result, the substantially L-shaped member 61 is enabled to form a new path D inside the primary bag B1 from outside. In this case, the position (height) of the second pressing member is not limited particularly.

Now, the operation of the second embodiment will be explained.

So long as a given liquid, for example, blood is normal, the substantially L-shaped members 61, 61 disposed one each on the front and rear surface sides of the primary bag B1 are moved toward each other and enabled to compress the primary bag B1 when the handle H is rotated after the timer T has been started, the information on operation displayed, and the door shut.

The pair of platelike first pressing members 65 are moved to the position on the extension of the terminal of the seal portion d provided in the primary bag B1 and the first pressing members 65 are then advanced through the reciprocating block 67 by the operation of the cylinder member 68 so as to compress the front and rear surface sides of the primary bag B1. This compression results in the formation of a path D capable of guiding the component of the red blood cell layer S2 through the second outlet Q2. In this case, since the second pressing member 66 presses itself against the front surface side of the primary bag B1 and the rear surface side, the lower end of the first pressing member 65 is desired to be positioned at a level within the size of the plasma layer S1.

Then, the pressing body 60 urged by the spring member S exerts pressure on the front surface of the primary bag B1 so as to guide the components such as of the red blood cell layer S2 out via the tubes t1, t2.

Since the path D for guiding the component of the red blood cell layer S2 is formed from outside in consequence of the tight adhesion of the front and rear surface sides of the primary bag B1 as described above, the path D is enabled to effect the extraction of the component of the desired layer easily without reference to the type of container or without regard to what position the intermediate layer S3 assumes in the primary bag B1.

When the substantially L-shaped member 61 which is integrally composed of the first pressing member 65 and the second pressing member 66 is pressed against the primary bag B1 and moved per se in the horizontal direction from the lateral end part of the primary bag B1 to the position between the first outlet Q1 and the second output Q2, the path D is collapsed and the liquid is expelled therefrom. No liquid component is present any more in the path D. Thus, the formation of the path D can be attained simultaneously with the discharge of the intermediate layer B3 which is not desired to flow out. When the compression causing the collapse is released, the plasma layer S1 and the red blood cell layer S2 can be easily collected fractionally through the first outlet Q1 and the second outlet Q2, depending on the position of the intermediate layer B3.

In the embodiment described above, the substantially L-shaped member 61 may press on only one side instead of both sides of the parent container. The first pressing member 65 and the second pressing member 66 are not always required to be integrally formed.

Now, the third embodiment of this invention will be explained below.

Figure 16:
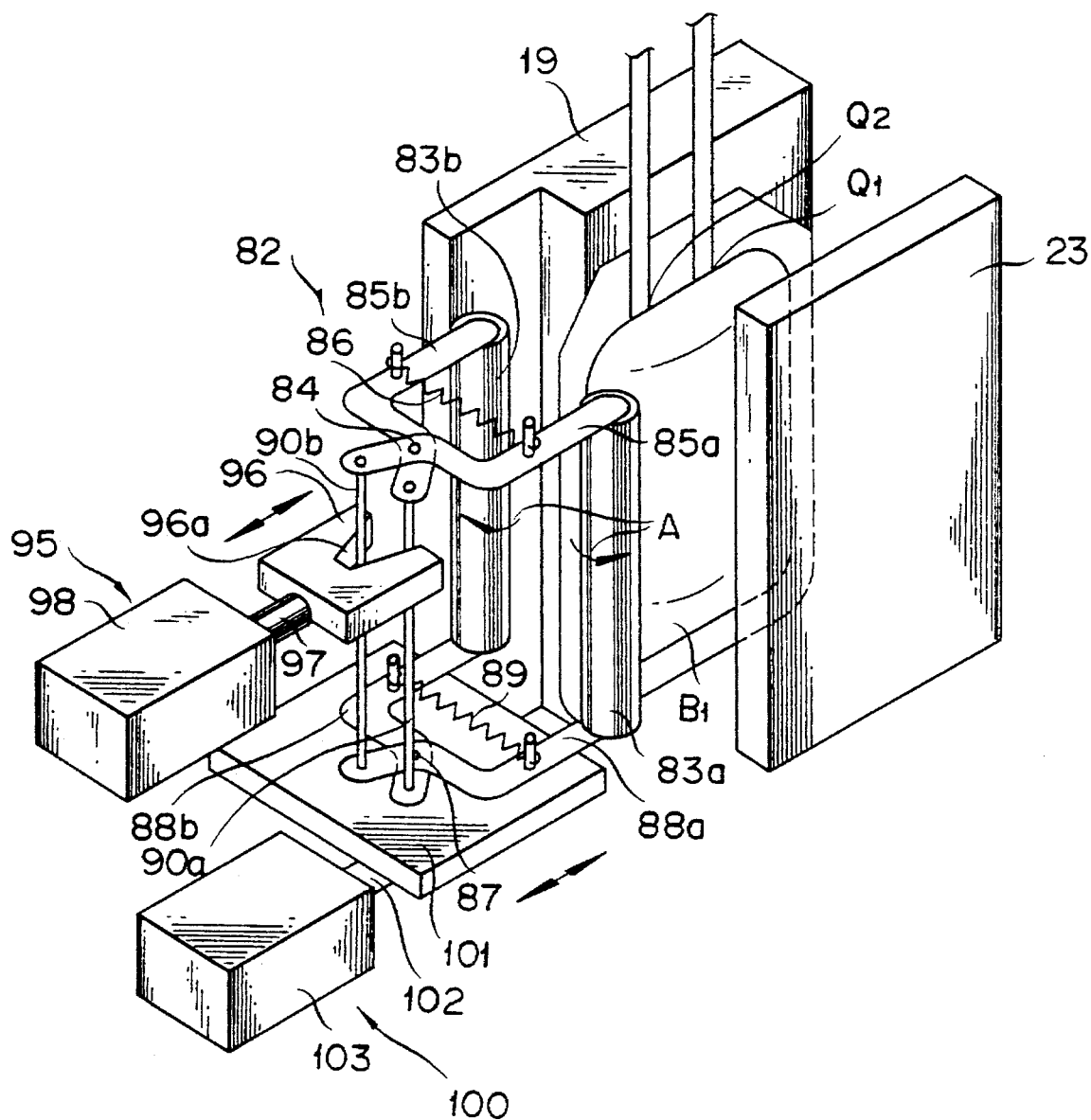
FIG. 16 is a schematic perspective view of a liquid separating apparatus according with the third embodiment of this invention.

The pressing member of the present embodiment, as shown in FIG. 16, comprises a depressing part 82 which is composed of two rollers (roller type depressing members) 83a, 83b set in place in the front lateral part of the main body case 14 and adapted to depress the primary bag B1 so as to form a tightly adhering portion on the front and rear surface sides of the primary bag B1, roller switching means 95 which causes the roller type depressing members 83a, 83b to be moved toward or away from each other, roller moving means 100 which causes the depressing part 82 to be laterally moved toward or away from the primary bag B1, and a pressing plate 23 which exerts pressure on the front surface side of the primary bag B1.

The depressing part 82 is provided with two rollers 83a, 83b provided therein with built-in motors for imparting rotation to the rollers and disposed in the vertical direction. The upper end parts of the rollers 83a, 83b are rotatably connected to one end respectively of the first upper lever 85a and the second upper lever 85b which are rotatably connected to each other through a pin 84. The lower end parts of the rollers 83a, 83b are rotatably connected to one end respectively of the first lower lever 88a and the second lower lever 88b through a pin 87. The other ends of the first upper lever 85a and the first lower lever 88a are supported fast by a strut 90a disposed vertically. The other ends of the second upper lever 85b and the second lower lever 88b are likewise supported fast by a strut 90b disposed vertically. Spring members 86, 89 are also provided which impart forces to the first lever and the second lever so that their respective leading end parts will move away from each other. Thus, the rollers 83a, 83b are constantly kept at separated positions. By the use of the roller switching means 95, however, the rollers 83a and 83b can be moved toward each other so as to bring parts of the front and rear surface sides of the primary bag B1 into tight contact with each other, divide the liquid stored in the primary bag B1 into two regions and, at the same time, give rise to a path D for guiding the liquid of the lower layer S2 to the second outlet Q2 formed in the primary bag B1.

The roller switching means 95 mentioned above is provided with a substantially V-shaped body 96 having a substantially V-shaped groove formed at the leading end thereof. To the end part of the V-shaped body 96 is connected a reciprocating bar 97. A solenoid (depressing means) 98 is provided which serves the purpose of moving the reciprocating bar 97 back and forth. The rollers 83a and 83b are moved toward each other by pressing the inclined surfaces 96a of the V-shaped groove of the V-shaped body 96 against the struts 90a, 90b mentioned above thereby causing the struts 90a and 90b to move toward each other.

The roller switching means 95 is supported on a base plate 101 by means of a supporting member which is not shown in the diagram. The roller moving member 100 is connected to the base plate 101 adapted to support the depressing member 82 mentioned above. A reciprocating bar 102 is connected to a connecting member (not shown) disposed in the bottom part of the base plate 101. A solenoid (depressing means) 103 is provided which plays the part of moving the reciprocating bar 102 back and forth. As a result, the depressing part 82 can be moved toward or away from the primary bag B1 from the lateral side and brought to a stop at the prescribed position.

The construction for moving the rollers 83a and 83b toward or away from each other does not need to be limited to what has been described above but may be suitably altered. The drive sources for the roller switching means 95 and the roller moving means 100 are not particularly limited to solenoids. Motors or cylinders may be used instead.

Now, the operation of the third embodiment will be explained below.

So long as a given liquid such as blood is normal, the timer T is started, the information on the operation is displayed, and the door is shut in the same manner as described above. By rotating the handle H subsequently, the solenoid 98 is actuated to push the reciprocating bar 97 outward as illustrated in FIG. 16 and press the inclined surfaces 96a of the V-shaped groove of the V-shaped body seated at the leading end of the reciprocating bar 97 against the struts 90a, 90b, with the result that the struts 90a, 90b are moved toward each other as gradually nipped jointly between the tapering walls of the V-shaped grove of the V-shaped body. As a result, the struts 90a, 90b and the rollers 83a, 83b disposed at the other ends on the opposite side move toward each other and eventually come into tight contact. With the apparatus now in the state on the operation described above, the motors contained in the rollers 83a, 83b are actuated to rotate the rollers in the direction A shown in FIG. 16 and, at the same time, the solenoid 103 is set operating to propel the reciprocating bar 97 outward and cause the depressing part 82 supported on the base plate 101 to approach laterally the primary bag B1. As a result, the two rollers 83a, 83b are caused, as illustrated in FIG. 17, to advance on parts of the front and rear surface sides of the primary bag B1 from the lateral end part thereof while continuously exerting pressure, namely imparting a squeezing motion, thereon and consequently allowing the parts to form a tightly adhering part. Eventually, they are brought to a stop at the prescribed position as shown in FIG. 18. In consequence of the operation just described, the liquid stored in the primary bag B1 can be divided into two regions and, at the same time, the path D for guiding the lower layer S2 to the second outlet Q2 formed in the primary bag B1 can be formed.

Then, the pressing plate 23 which is urged by the spring member S exerts pressure on the front surface of the primary bag B1 and consequently guides the component of the red blood cell layer S2 through the tubes t1, t2 into the exterior.

In the case of the present embodiment, since the continued pressurization by the rollers is utilized, the possibility of the intermediate layer S3 being pushed away by the motion of the rollers and forced to flow around on the side opposite to the rollers on the left in the bearings of the diagram can be precluded. Thus, the accuracy for the separation of components is notably improved.

Since the lower end parts of the rollers 83a, 83b are positioned at levels higher than that of the lower end part of the primary bag B1 as shown in FIGS. 17 and 18, the path D formed as described above communicate with the lower layer S2. To secure the communicating part between the path D and the lower layer S2 as described above, the lower end parts of the rollers 83a, 83b are desired to be positioned at levels higher than that of the lower end part of the primary bag B1. Incidentally, the position at which the intermediate layer S3 is formed is not constant. When the lower end parts of the rollers 83a, 83b are positioned at levels higher than the level of the primary bag B1, the liquid of the intermediate layer S3 takes its own course of entering the path D during the liquid transfer of the lower layer S2 through the path D to the second outlet Q2. Thus, the lower end parts of the rollers 83a, 83b are desired to be positioned at the lowest possible levels on the condition that the communicating part between the path D and the lower layer S2 should be secured.

Figure 17A:
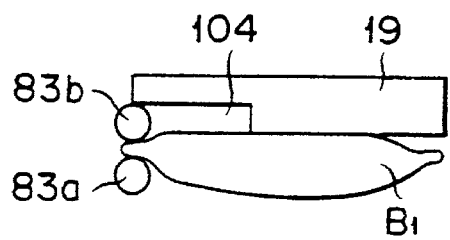
FIG. 17 A and B are respectively a plan view and a front view illustrating schematically the initial stage of pressurization by the use of a roller.
Figure 18A:
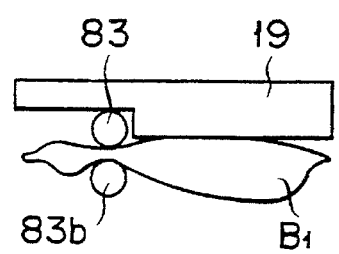
FIG. 18 A and B are respectively a plan view and a front view illustrating schematically the final stage of pressurization by the use of a roller.
Figure 17B:
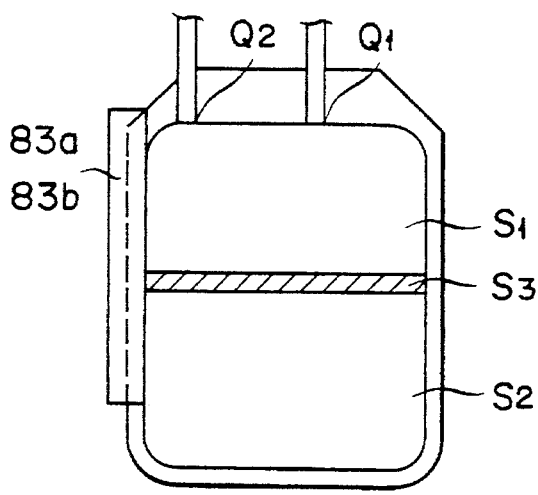
Figure 18B:
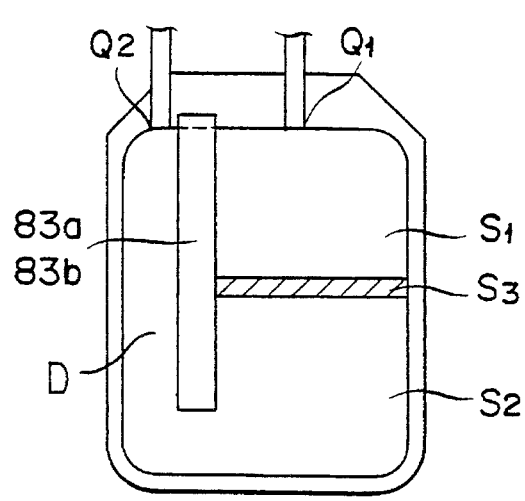

Further, in the case of the present embodiment, since the depressing part 82 is provided with two rollers and the rollers are adapted to advance on the primary bag B1 while continuously pressing on the front and rear surface sides simultaneously, a relief 104 for admitting the roller 83b is formed in part of the lateral side of the supporting member 19 as shown in FIG. 17A.

Figure 19A:
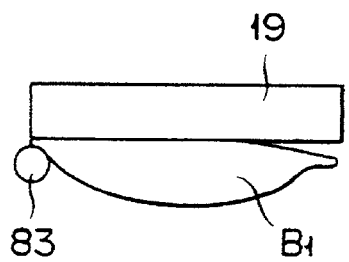
FIG. 19 is a schematic plan view illustrating a modified example of the operation of the roller; the part A representing a schematic plan view illustrating the initial stage of pressurization and the part B a schematic plan view illustrating the final stage of pressurization.
Figure 19B:
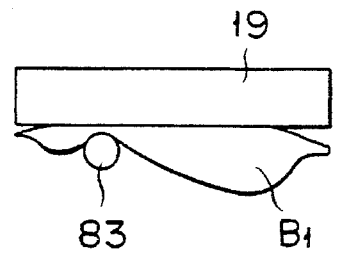

The number of the rollers mentioned above are not limited to 2. One roller may suffice at times. In this case, the roller 83 may be pressed against the supporting member 19 and per se advanced thereon as shown in FIG. 19.

After the path D for guiding the liquid of the lower layer S2 to the second outlet Q2 has been formed on one lateral side member of the primary bag B1, the container pressing part 13 is actuated and caused to press on the primary bag B1 as in the case of the embodiment cited above.

The embodiments cited above represent cases effecting fractional collection of the blood components by the use of a blood bag. This invention is not limited to this particular mode of liquid collection. It can be embodied in the fractional collection of various liquids.

Figure 20:
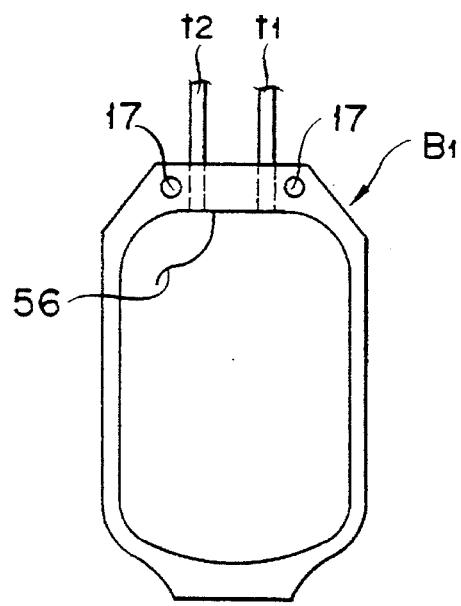
FIG. 20 is a front view illustrating a modified example of primary bag.
Figure 21:
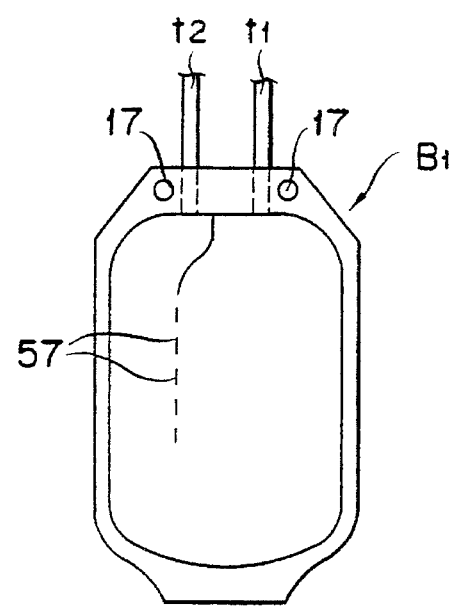
FIG. 21 is a front view illustrating another modified example of primary bag.
Figure 22:
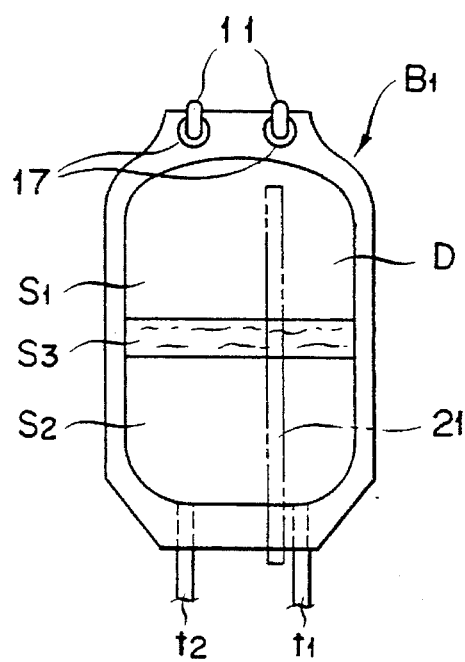
FIG. 22 is a front view illustrating the primary bag retained in another mode of retention.

In the embodiments cited above, the primary bag in all of the blood bags which are used for collecting blood may be sealed only in the neighborhood of the apex and provided in advance with a path 56 as illustrated in FIG. 20 or may have a fragmentally adhering part 57 formed as by fusion of the front and rear surface sides in the part destined to be tightly joined by the pressure of the pressing member as shown in FIG. 21. It is further permissible to have the primary bag B1 retained by the use of hooks 11, ie. a container retaining member, in such a manner that the outlets to which the tubes t1, t2 are connected will be positioned on the lower side as shown in FIG. 22. With the primary bag B1 held in the state mentioned above, the communicating portion of the path D is formed in the upper part of the primary bag B1 as by the use of the pressing member 21 as shown with two-dot chain line in FIG. 13 and the component of the upper layer S1 is fated to be extracted from the lower side.

Figure 23:
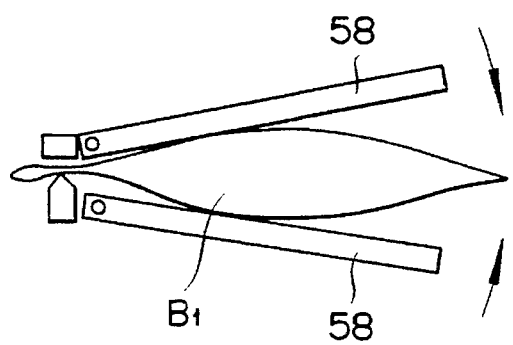
FIG. 23 is a plan view illustrating another mode of pressurization on the bag.

It is also permissible to adopt a pressing method which effects desired pressurization on the primary bag B1 by driving both of the pressing plates 58 disposed on the opposite sides of the primary bag B1 as shown in FIG. 23 and consequently enabling them to exert pressing force thereon.

We claim:

1. A liquid separating apparatus comprising a container retaining member for retaining a flexible container having first and second outlets at one end and storing therein liquid components fractionated into at least three layers that include an upper layer, an intermediate layer and a lower layer, a container pressing part that includes a supporting member for supporting one of two opposite surfaces of the container retained by said container retaining member and a pressing member for pressing said container, said pressing member including a substantially L-shaped pressing member and a second pressing member disposed in contiguous relation to the substantially L-shaped pressing member, drive means connected to the substantially L-shaped pressing member for driving the substantially L-shaped pressing member into pressing engagement with the container to maintain said at least three layers intact while also forming a tightly adhering portion on the opposite surfaces of the container which extends from between the first and second outlets across the intermediate layer to a position spaced from an end of the container opposite said one end to form within said container a large volume portion communicating with said first outlet and a small volume portion communicating with said second outlet, said substantially L-shaped pressing member being supported for rotation about an axis, said substantially L-shaped pressing member being rotated by the drive means about said axis to move a leg of said substantially L-shaped pressing member which intersects said axis and form a path between said large volume portion and said small volume portion.

2. A liquid separating apparatus according to claim 1, wherein the substantially L-shaped pressing member includes a lower end part that is adapted to be positioned at a level higher than the level of the opposite end of said container.

3. A liquid separating apparatus according to claim 1, including means for reciprocating said substantially L-shaped pressing member in a vertical direction.

4. A liquid separating apparatus according to claim 1, wherein said container pressing member is disposed inside a housing, the supporting member being a door which is mounted on the housing for swinging movement.

5. A liquid separating apparatus according to claim 1, wherein said container pressing part includes a pressing body.

6. A liquid separating apparatus according to claim 1, including a spring connected to the pressing body for urging the pressing body towards the supporting member.

* * * * *